(12) United States Patent
Sams et al.

(10) Patent No.: US 10,549,043 B2
(45) Date of Patent: Feb. 4, 2020

(54) SYRINGE DRIP GUARD

(71) Applicant: BAYER HEALTHCARE LLC, Whippany, NJ (US)

(72) Inventors: Stephen Sams, Bassingbourn (GB); Gerald W. Callan, Cranberry Township, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 269 days.

(21) Appl. No.: 15/317,241

(22) PCT Filed: Jun. 8, 2015

(86) PCT No.: PCT/US2015/034687
§ 371 (c)(1),
(2) Date: Dec. 8, 2016

(87) PCT Pub. No.: WO2015/191454
PCT Pub. Date: Dec. 17, 2015

(65) Prior Publication Data
US 2017/0113004 A1    Apr. 27, 2017

Related U.S. Application Data

(60) Provisional application No. 62/010,223, filed on Jun. 10, 2014.

(51) Int. Cl.
*A61M 5/31* (2006.01)
*A61M 5/00* (2006.01)
*A61M 5/145* (2006.01)

(52) U.S. Cl.
CPC .......... *A61M 5/3134* (2013.01); *A61M 5/007* (2013.01); *A61M 5/3129* (2013.01);
(Continued)

(58) Field of Classification Search
CPC ...... A61M 5/3134; A61M 5/178; A61M 5/31; A61M 2005/314
See application file for complete search history.

(56) References Cited

U.S. PATENT DOCUMENTS 1,553,710 A * 9/1925 Muus ................. A46B 11/0093
15/248.1
1,934,046 A * 11/1933 Demarchi ............. A61M 5/425
604/115

(Continued)

FOREIGN PATENT DOCUMENTS

EP          2243505 A3    3/2011
WO      2011011396 A1    1/2011

OTHER PUBLICATIONS

"Extended European Search Report from EP Application No. 15806991", Mar. 14, 2018.

(Continued)

*Primary Examiner* — Nilay J Shah
(74) *Attorney, Agent, or Firm* — David Schramm; Joseph L. Kent; James R. Stevenson (57) ABSTRACT

A syringe assembly may include a syringe having a distal end, a proximal end, and a sidewall extending between the distal end and the proximal end, and a syringe drip guard extending around at least a circumferential portion of the sidewall between the distal end and the proximal end of the syringe. The syringe drip guard may have an outer wall protruding radially outward relative to the sidewall. A channel may be defined between the outer wall of the syringe drip guard and the sidewall of the syringe. The channel may have a closed proximal end and an open distal end. The syringe drip guard may be configured to at least one of: collect, absorb, or adsorb fluid within the channel.

6 Claims, 6 Drawing Sheets

(52) U.S. Cl.
CPC ....... *A61M 5/14546* (2013.01); *A61M 5/3146* (2013.01); *A61M 2005/3142* (2013.01); *A61M 2209/00* (2013.01)

(56) References Cited

U.S. PATENT DOCUMENTS

| | | | | |
|---|---|---|---|---|
| 2,394,640 | A | * | 2/1946 | Singer ................ A46B 11/0093 15/248.1 |
| 4,907,968 | A | | 3/1990 | Eisner et al. |
| 5,002,533 | A | | 3/1991 | Jullien |
| 5,290,255 | A | * | 3/1994 | Vallelunga .......... A61M 5/3271 604/110 |
| 5,324,527 | A | * | 6/1994 | Coleman ................ A23G 3/563 426/110 |
| 5,527,297 | A | | 6/1996 | Paul |
| 6,050,981 | A | | 4/2000 | Lampropoulos et al. |
| 6,179,019 | B1 | * | 1/2001 | Gowans ................... C25C 7/06 141/1 |
| 6,537,257 | B1 | * | 3/2003 | Wien .................. A61M 5/3202 604/198 |
| 7,419,478 | B1 | | 9/2008 | Reilly et al. |
| 7,666,169 | B2 | | 2/2010 | Cowan et al. |
| 9,173,995 | B1 | | 11/2015 | Tucker et al. |
| 9,199,033 | B1 | | 12/2015 | Cowan et al. |
| 2005/0251096 | A1 | | 11/2005 | Armstrong et al. |
| 2006/0069347 | A1 | | 3/2006 | Besing |
| 2007/0189924 | A1 | | 8/2007 | Knight |
| 2008/0287885 | A1 | * | 11/2008 | Hoffmann ........... A61M 5/3129 604/222 |
| 2014/0066894 | A1 | | 3/2014 | Pearce et al. |

OTHER PUBLICATIONS

"International Preliminary Report on Patentability from PCT Application No. PCT/US2015/034687", Dec. 22, 2016.

* cited by examiner

SYRINGE DRIP GUARD

CROSS-REFERENCE TO RELATED APPLICATION

This application is a U.S. national stage filing under 35 U.S.C. § 371 of International Application No. PCT/US2015/034687, filed Jun. 8, 2015, which claims the benefit of U.S. Provisional Patent Application No. 62/010,223, filed Jun. 10, 2014, the disclosure of which is incorporated by reference in its entirety.

BACKGROUND OF THE INVENTION

Field of the Invention

The present disclosure is related to the medical field and, more particularly, to a syringe used in the medical field where the syringe includes a drip guard configured to absorb and/or collect fluids that may drip or leak from the syringe.

Description of Related Art

A number of injector-actuated syringes and powered injectors for use in medical procedures have been developed. Typically, such injectors have drive members, such as pistons, that connect to a syringe plunger. The syringe generally includes a barrel with the syringe plunger being slidably disposed within the barrel. The drive members are configured for driving the plungers in a proximal and/or distal direction relative to a longitudinal axis of the barrel to aspirate a fluid into the syringe barrel and/or deliver the fluid from the syringe barrel.

During the priming of the syringe or the delivery of the fluid from the syringe barrel, the medical fluid may drip or leak from the tip of the syringe. Such dripping or leaking results in uncleanliness and hazardous waste issues and, in certain cases, the fluid leakage down the syringe and into the injector casing may cause the injector to seize or otherwise malfunction during operation creating the need for more frequent servicing or replacement of the injector components. Conventional methods of absorbing or collecting the leaked medical fluid include the use of a drip flange positioned on an outer surface of the barrel of the syringe. These drip flanges may prevent leakage of fluids into the injector but can also significantly increase the width of the syringe, which results in increased packaging size, packaging costs, and potential rupturing of the packaging during shipment. Conventional drip flanges are also limited by the direction of draw and the material choice for the injection molding of the syringes. Further, certain current drip flanges are formed as flat ledges that extend perpendicularly from the barrel of the syringe. One disadvantage with these types of drip flanges is the inability of the drip flange to trap or hold liquid that may leak from the syringe. The leaked fluid often is directed away from the barrel of the syringe to another part of the powered injector.

Although substantial advances have been made in the design of syringes, it remains desirable to develop improved designs and methods to absorb and/or collect fluid that may drip or leak from an injector, syringe, or syringe assembly.

SUMMARY OF THE DISCLOSURE

The present disclosure generally relates to syringe assemblies and to methods of absorbing and/or collecting fluids leaked from the syringe assemblies and/or preventing the fluids from fouling the interior workings of a power injector. Further, the syringe assemblies described herein have improved configurations for packaging and shipping.

In one aspect, a syringe assembly is disclosed. The syringe assembly may include a syringe having a distal end, a proximal end, and a sidewall extending between the distal end and the proximal end, and a syringe drip guard extending around at least a circumferential portion of the sidewall between the distal end and the proximal end of the syringe. The syringe drip guard may have an outer wall protruding radially outward relative to the sidewall. A channel may be defined between the outer wall of the syringe drip guard and the sidewall of the syringe. The channel may have a closed proximal end and an open distal end. The syringe drip guard may be configured to at least one of collect, absorb, and adsorb fluid within the channel.

The outer wall of the syringe drip guard may extend from the proximal end to the distal end of the syringe such that the outer wall is angled relative to a longitudinal axis of the syringe or the outer wall is substantially parallel to the longitudinal axis of the syringe. The syringe drip guard may have a bottom surface that connects a proximal end of the outer wall to the sidewall of the syringe. An inner top edge of the outer wall of the syringe drip guard may be beveled toward the channel. An adsorbent material may be located within the channel for adsorbing fluid within the channel. The syringe drip guard may be made from a plastic material. The syringe drip guard may be made from a flexible material. The syringe drip guard may be circular in shape. The syringe drip guard may be fixed on the sidewall of the syringe via a friction fit. The syringe drip guard may be monolithically formed with the sidewall of the syringe.

In another aspect, another syringe assembly is disclosed. The syringe assembly may include a syringe having a distal end, a proximal end, and a sidewall extending between the distal end and the proximal end, and a syringe drip guard extending around at least a circumferential portion of the sidewall between the distal end and the proximal end of the syringe. The syringe drip guard may have an outer wall, an inner wall, and a bottom surface connecting a proximal end of the outer wall with a proximal end of the inner wall. A channel may be defined between the outer wall and the inner wall of the syringe drip guard. The channel may have a closed proximal end and an open distal end. The syringe drip guard may be configured to at least one of collect, absorb, and adsorb fluid within the channel.

The outer wall of the syringe drip guard may extend from the proximal end to the distal end of the syringe such that the outer wall is angled relative to a longitudinal axis of the syringe or the outer wall is substantially parallel to the longitudinal axis of the syringe. At least one of an outer top edge of the inner wall and an inner top edge of the outer wall of the syringe drip guard may be beveled toward the channel. An adsorbent material may be located within the channel for adsorbing fluid within the channel. The syringe drip guard may be made from a plastic material. The syringe drip guard may be made from a flexible material. The syringe drip guard may be circular in shape. The syringe drip guard may be fixed on the sidewall of the syringe via a friction fit. The syringe drip guard may be monolithically formed with the sidewall of the syringe.

In another aspect, a drip guard for a syringe is disclosed. The drip guard may include an outer wall having a proximal end and a distal end, and a bottom surface extending from the proximal end of the outer wall. The outer wall and the bottom surface may define a channel. The channel may have a closed proximal end and an open distal end. The syringe drip guard may be configured to at least one of: collect, absorb, or adsorb fluid within the channel.

The outer wall may be angled relative to the bottom surface or may be substantially perpendicular to the bottom surface. Alternatively, the bottom surface may have a generally concave cross-section. The drip guard may include an inner wall having a proximal end and a distal end. The bottom surface may connect the proximal end of the outer wall with the proximal end of the inner wall. The outer wall, the bottom surface, and the inner wall may define the channel. At least one of an outer top edge of the inner wall and an inner top edge of the outer wall of the syringe drip guard may be beveled toward the channel. An adsorbent material may be located within the channel for adsorbing fluid within the channel. The syringe drip guard may be made from a plastic material. The syringe drip guard may be made from a flexible material. The syringe drip guard may be circular in shape and configured to fit around the outer circumference of a syringe barrel, for example, by a friction fit or configured to be adhered to the outer circumference of the syringe barrel.

In another aspect, another syringe assembly is disclosed. The syringe assembly may include a syringe having a distal end, a proximal end, and a sidewall extending between the distal end and the proximal end, and a fluid drip trap positioned on the distal end of the syringe. The fluid drip trap may include a wall that extends distally and circumferentially around the distal end of the syringe. A seal may be created between the distal end of the syringe and the wall of the fluid drip trap to at least one of collect, absorb, or adsorb fluid that leaks or drips from the distal end of the syringe. The fluid drip trap may also include a cover provided on a distal surface of the wall. The fluid drip trap may be positioned on the distal end of the syringe via a friction fit or may be adhered or welded to the distal end of the syringe. An adsorbent material may be located within the fluid drip trap to adsorb any medical fluid that leaks out of the distal tip of the syringe.

Further details and advantages of various aspects described in detail herein will become clear upon reviewing the following detailed description of the various aspects in conjunction with the accompanying figures.

DESCRIPTION OF THE DISCLOSURE

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and description provided herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the figures. The term "proximal" refers to the direction towards the injector assembly or device and away from the patient. The term "distal" refers to the outward direction extending away from the injector assembly or device and toward the patient. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structure, construction, and method of operation, and many advantages may be understood and appreciated.

Figure 1:
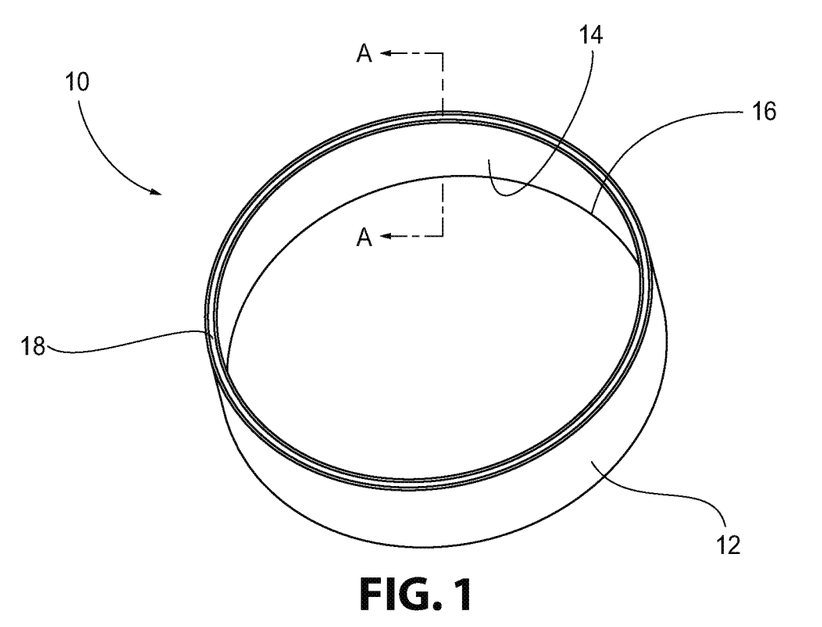
FIG. 1 is a perspective view of a syringe drip guard according to one aspect of this disclosure.

FIG. 1 illustrates an aspect of a syringe drip guard 10 adapted to interface with a syringe 100 (shown in FIG. 5) of a fluid delivery system, such as a powered medical injector (not shown). The syringe may be fluidly connected to a source of fluid (not shown), where the fluid may be any desired medical fluid, such as saline, contrast, cell cultures, biologics, etc. Further description of the use of the drip guard 10 in conjunction with a syringe is described herein.

Figure 2:
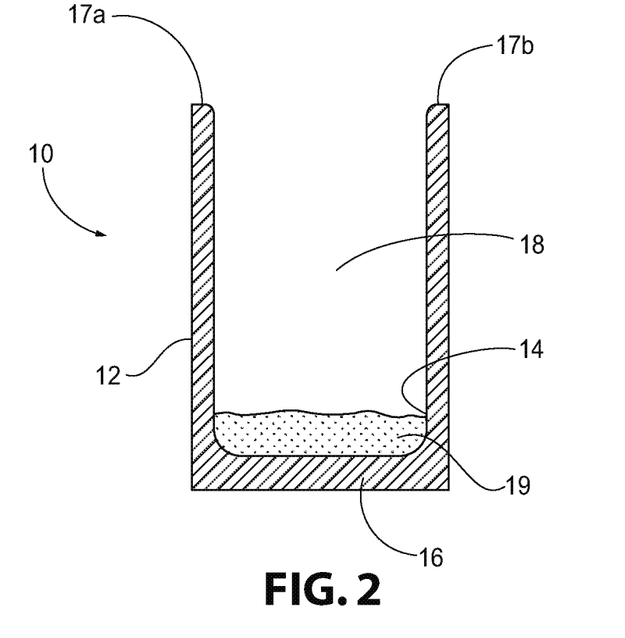
FIG. 2 is a cross-sectional view of the syringe drip guard of FIG. 1 along line A-A.

Referring to FIGS. 1 and 2, in one aspect, the drip guard 10 may include an outer wall 12, an inner wall 14, and a radial bottom surface 16. The outer wall 12 and the inner wall 14 are connected to one another via the bottom surface 16. The outer wall 12 and the inner wall 14 define a channel 18 therebetween with the bottom surface 16 enclosing a lower portion of the channel 18. According to one embodiment, the outer wall 12 and the inner wall 14 may be substantially parallel. According to another embodiment the outer wall 12 may be angled relative to the inner wall 14. The drip guard 10 may be circular in shape, designed to fit around the circumference of a syringe body. However, it is also contemplated that alternative shapes may be used, such as polygonal including triangular or trapezoidal, or oval as required by the shape of the syringe. The thickness of the drip guard 10, i.e., the radial distance from the outer wall 12 to the inner wall 14 is considerably thin, for example, from 0.5 mm to 10 mm, so as to reduce the overall diameter of the syringe assembly when the drip guard 10 is positioned thereon. One or both of the top edges 17a, 17b of the outer wall 12 and the inner wall 14, respectively, may be beveled toward channel 18 to assist in the collection of fluid in the channel 18 of the drip guard 10. In another aspect, an inner top edge 17a of the outer wall 12 may be beveled. In one aspect, an outer top edge 17b of the inner wall 14 may be beveled to guide fluid into the channel 18.

In one aspect, the channel 18 may extend around the entire circumference of the drip guard 10. However, it is also contemplated that the channel 18 may only be defined in certain portions of the drip guard 10 so that the drip guard 10 includes solid portions or braces positioned in between portions that define respective channels 18. In various aspects, the solid portions may increase the structural integrity of the drip guard 10. As shown in FIG. 2, the cross-section of channel 18 may be U-shaped. However, it is to be understood that alternative shapes for the channel 18 may be used, such as polygonal including rectangular, square, triangular, and trapezoidal-shaped cross-sections, among others. For example, in certain aspects, the drip guard 10 of the present disclosure may include outer wall 12 and inner wall 14, but may lack bottom surface 16, such that a bottom portion of the outer wall 12 connects directly to a bottom portion of inner wall 14. According to this aspect, the channel 18 may have a triangular cross-section or an arcuate cross-section. In one aspect, the channel 18 may be V-shaped.

In certain embodiments, the outer wall 12 may include a radial wall or baffle (not shown) on an inner surface of the outer wall 12 that partially extends into channel 18. The radial wall may be generally perpendicular to the surface of the inner surface or may be angled toward the proximal end relative to the longitudinal access of the drip guard 10. According to these embodiments, drip guard 10 is configured to capture fluid drips that flow down the exterior surface of a syringe barrel while the syringe is held in a generally vertical direction, for example during loading of the syringe with fluid. Subsequently, the syringe and injector may be rotated to a generally downwardly angled direction during an injection procedure. Gravitational forces on the fluid within the drip guard 10 may then cause the fluid to flow in a distal direction along the inner surface of the outer wall 12. The fluid flow may be impeded by the presence of the radial wall or baffle, thus preventing fluid from dripping out of drip guard 10 onto the injector or floor of the procedure room. Other embodiments of drip guard 10 may include a similarly configured wall or baffle extending from an inner surface of inner wall 14 into channel 18. The presence of one or both of the inner walls may also serve to maintain an adsorbent material 19 within the channel 18 of drip guard 10.

According to various aspects, the drip guard 10 may be fixed to a syringe sidewall 102 (shown in FIG. 5), for example, by molding, welding, or adhesive bonding, or may be removable from the syringe sidewall 102. In some aspects, the drip guard 10 may be monolithically formed with the sidewall 102 of the syringe 100. In one aspect, the drip guard 10 may be removably attached to a syringe 100 (FIG. 5) via an interference fit, a snap fit, or friction fit. In this aspect, any fluid drips or leaks are caught and/or absorbed in the drip guard 10. As fluid drips or leaks from a distal end 114 of the syringe 100 along a sidewall 102 of the syringe 100, the drip guard 10 may be configured to capture and/or absorb the leaked fluid. In particular, the fluid may be collected in the channel 18 of the drip guard 10. One advantage of this aspect of the drip guard 10 is the ability to collect and/or absorb the fluid in the channel 18 and then easily remove the drip guard 10 from a syringe without spilling the collected fluid. In certain aspects, channel 18 may include an adsorbent material 19 contained therein. Suitable adsorbent materials may include, for example, a sponge, foam, a fibrous material, an adsorbent or superadsorbent polymer, or the like. The adsorbent material 19 may be provided on the bottom surface 16 of the drip guard 10 or, alternatively, may be provided on each inner surface of the drip guard 10. The adsorbent material 19 may create adhesion between the molecules of the fluid and the drip guard 10.

Figure 3:
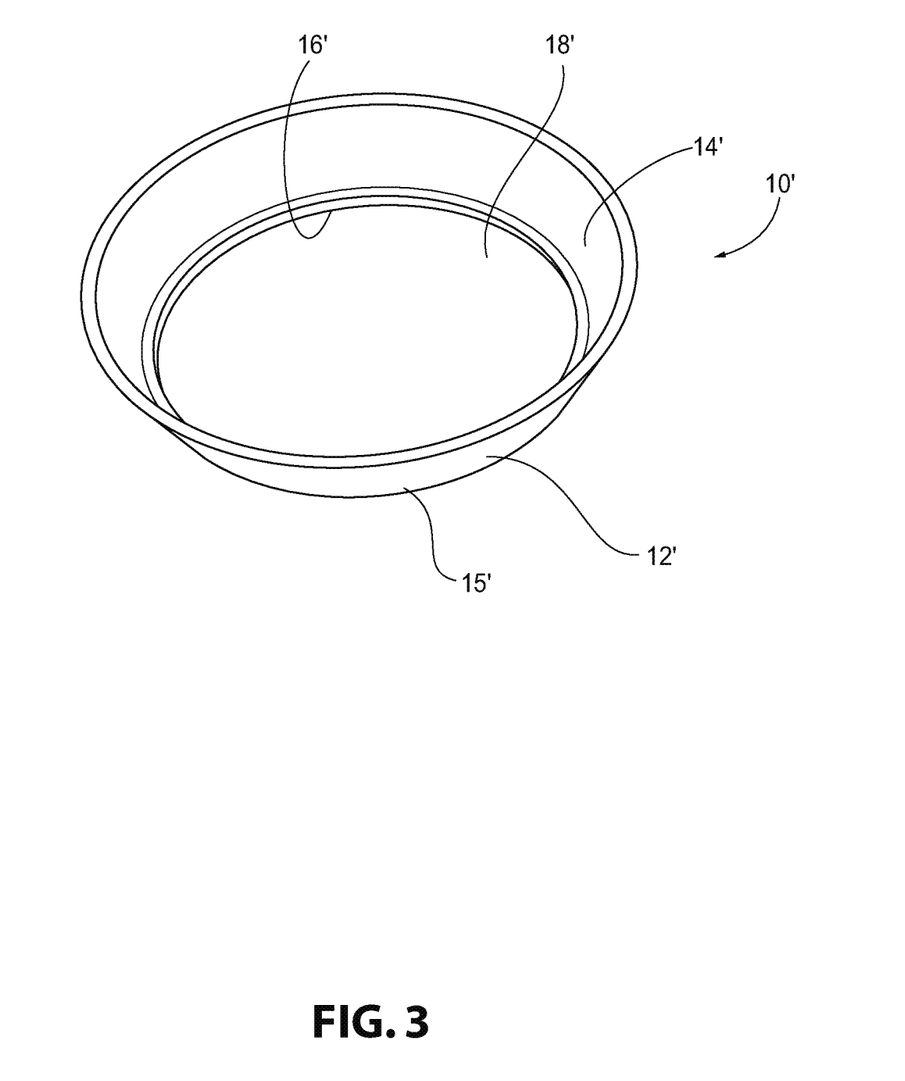
FIG. 3 is a top perspective view of another aspect of a syringe drip guard.
Figure 4:
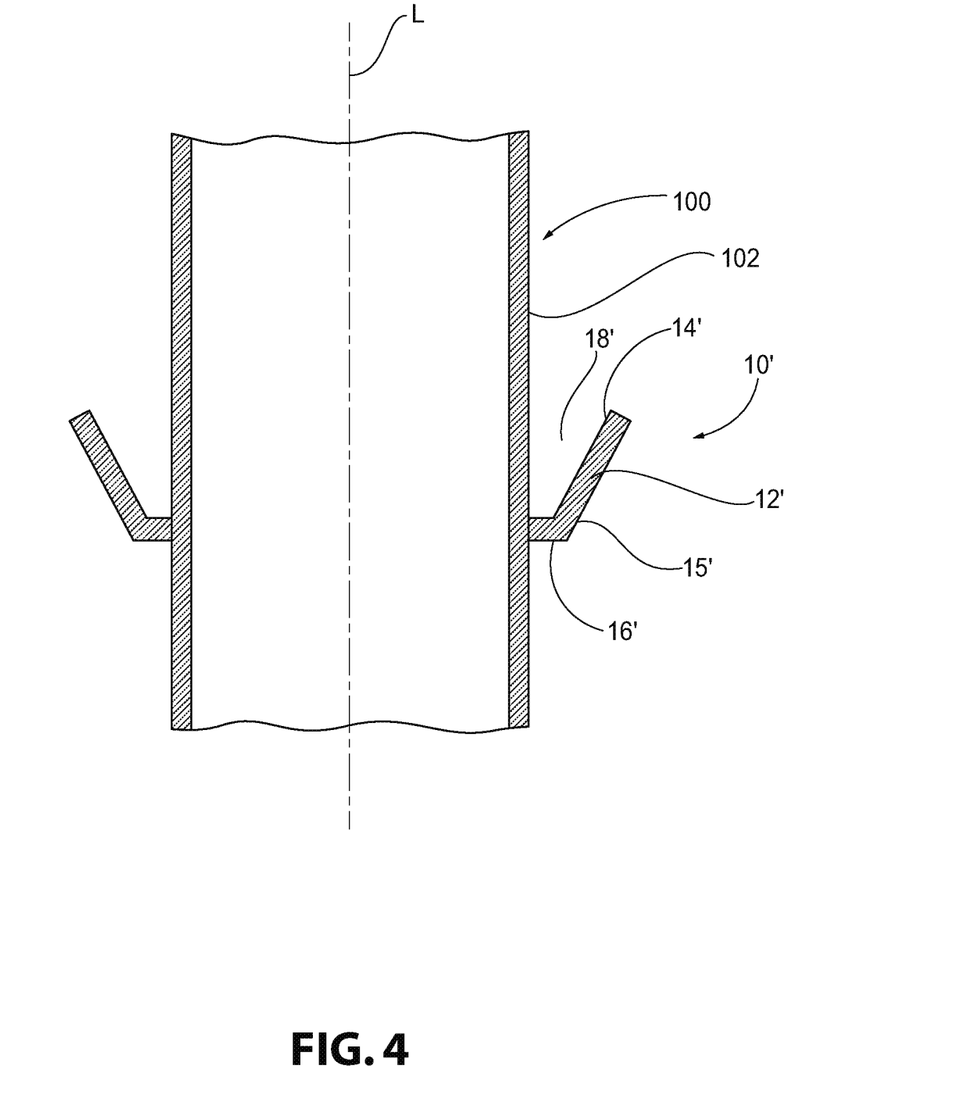
FIG. 4 is a cross-sectional view of the syringe drip guard of FIG. 3 as shown assembled on a syringe.

Referring to FIGS. 3 and 4, in another aspect, the drip guard 10' may include an outer wall 12', having an outer surface 15' and an inner surface 14', and optionally a bottom surface 16'. In this aspect, the outer wall 12' may be positioned at an angle relative to the bottom surface 16' or, alternatively, bottom surface 16' may be omitted and the outer wall 12' may be angled and attached directly to the outer surface of the syringe sidewall 102 at the lower, proximal edge of outer wall 12' such that the inner surface 14' of outer wall 12' and the syringe sidewall 102 come together to form a V-shaped channel 18. Further, when positioned on an outer surface of a syringe 100, the outer wall 12' may be positioned at an angle relative to the longitudinal axis L of the syringe 100. A channel 18' may be defined between the sidewall 102 of the syringe 100 and the inner surface 14' of the outer wall 12' of the drip guard 10'. Further, the channel 18' may be defined between the sidewall 102, inner surface 14' of outer wall 12' and the bottom surface 16'. According to various aspects, the drip guard 10' may be fixed to the syringe sidewall 102, for example, by molding, welding, or adhesive bonding, or in other aspects may be removably attached to the syringe sidewall 102. For example, in one aspect, the drip guard 10' may be removably attached to the syringe 100 via a snap fit (for example where the bottom surface 16' or the proximal edge of outer wall 12' snap into a circumferential groove in the syringe sidewall 102), an interference fit or friction fit. As fluid is dripped or leaked from the syringe 100 and drips or flows down the syringe sidewall 102, the drip guard 10' is configured to catch, collect and/or absorb the fluid, for example before the fluid flows into the interior mechanical workings of the injector or otherwise fouls an injector surface or drips on the floor of the procedure room. One advantage with this aspect of the drip guard 10' is the ability to allow the fluid to drip directly into the channel 18' of the drip guard 10', instead of contacting the inner wall 14 of the drip guard 10 and then dripping into the channel 18, as shown in FIG. 2.

The drip guard 10 may be formed from any suitable plastic or polymeric material, such as, but not limited to, nylon, polyvinyl polymers, polytetrafluoroethylene, polycarbonate, acrylic, or polyester, including medical grade and/or biodegradable versions of any thereof. However, alternative materials may be used to form the drip guard 10, including a flexible material such as rubber, which may allow for additional flexibility of the drip guard 10. In another aspect, the inner wall 14 may be thinner to allow a sealing member (not shown) to be positioned between the inner wall 14 and the syringe 100. The sealing member may be in the shape of a ring to extend around the outer circumferential surface of the syringe 100. In another aspect, the drip guard 10 may be formed from an absorbent material configured to improve the drip absorption of the drip guard 10. The absorbent material may be a 3-D foam, a sponge material, an adsorbent or superadsorbent polymer, fiber matrix, or a mesh material that includes a lattice-type structure. The mesh material may be configured to catch any drips that are leaked from the syringe 100 in between a plurality of mesh elements that create the lattice-type structure. By absorbing any drips or leaks from the syringe 100, the fluid is restricted from reaching the injector (not shown) connected to a proximal end of the syringe 100, which is advantageous, for example, in keeping the injector from becoming fouled or contaminated, seizing, malfunctioning, and/or requiring repairs before use of the syringe 100 may be resumed. It is also contemplated that the drip guard 10 may be formed from a hard plastic material or rubber, for example, with an absorbent material inserted into the channel 18 to absorb any drips or leaks that are directed into the drip guard 10. A sponge-like material may also be added into the channel 18 of the drip guard 10 to catch or absorb any leaked fluid.

Figure 5:
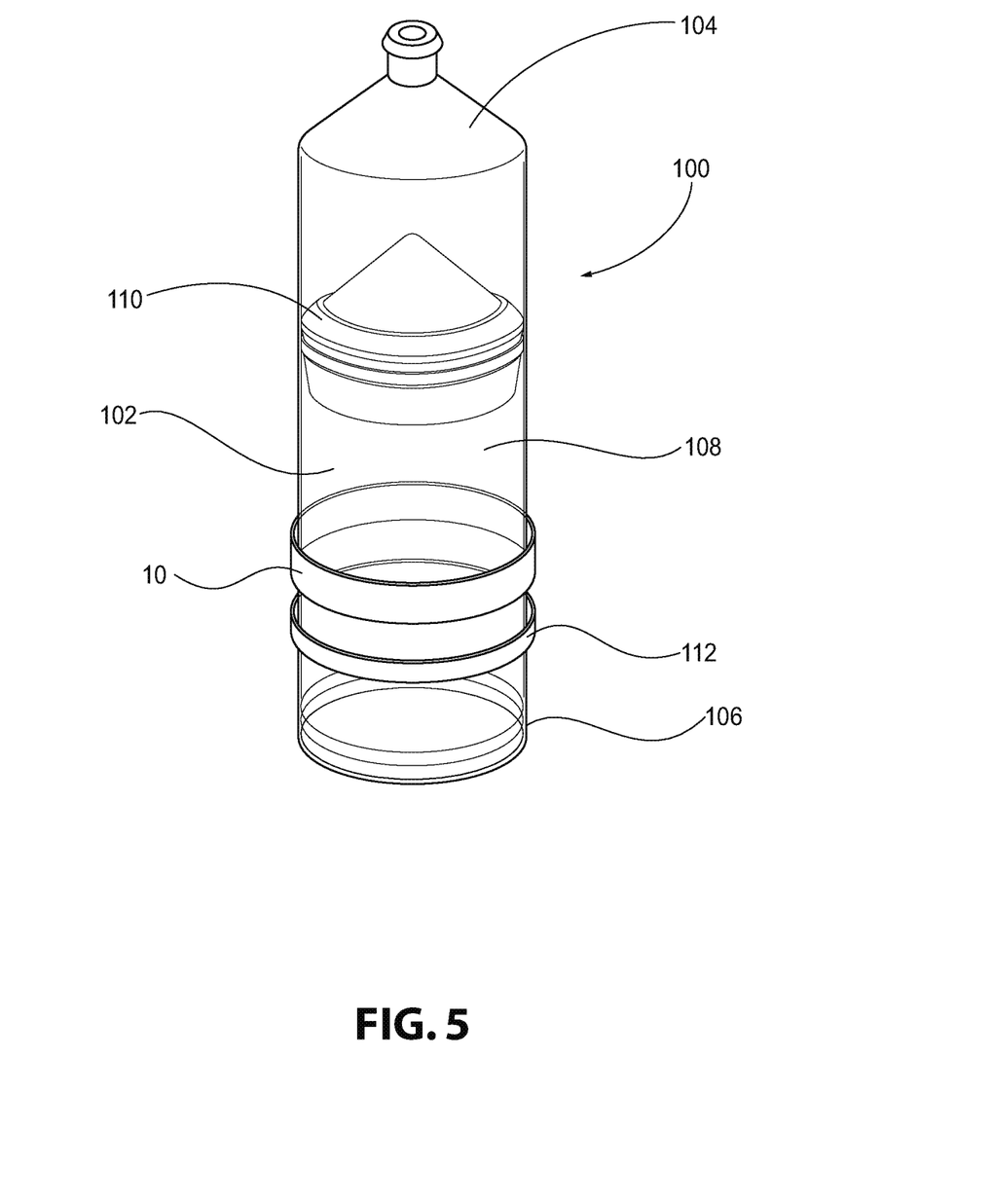
FIG. 5 is a perspective view of a syringe assembly including the syringe drip guard of FIG. 1.

Referring to FIG. 5, the drip guard 10 is configured to be positioned on a syringe 100. The syringe 100, which may also be referred to as a syringe assembly, includes a sidewall 102, a distal end 104, and a proximal end 106. The sidewall 102 extends between the distal end 104 and the proximal end 106 of the syringe 100. The sidewall 102 defines an interior volume 108 of the syringe 100. A plunger 110 may be disposed in the interior volume 108 of the syringe 100 and may be configured to aspirate or deliver medical fluid into or out of the syringe 100, respectively. An integral drip flange 112 may be positioned on the outer surface of the sidewall 102. The integral drip flange 112 provides additional collection and/or absorption of fluid that leaks from the syringe 100. The integral drip flange 112 is configured to divert any uncollected fluid from the drip guard 10 away from the injector, thereby keeping the injector dry, clean, and uncontaminated. One or more attachment features (not shown) may be located at the proximal end of syringe 100 to facilitate removable attachment of the syringe 100 to an injector interface.

With continued reference to FIG. 5, in certain aspects, the drip guard 10 may be molded or formed as a separate component from the syringe 100. The drip guard 10 may be assembled on the syringe 100 via an interference fit to create a fluid tight connection to the body of the syringe 100. The drip guard 10 may be attached to the syringe 100 at a manufacturing facility or the drip guard 10 may be shipped separately and attached to the syringe at the site where the injection procedure is to be performed. The drip guard 10 may be snap-fit, friction-fit or press-fit onto the syringe 100. The cross-sectional shape of the drip guard 10 (perpendicular to the longitudinal access of the syringe) corresponds to the longitudinal, cross-sectional shape of the syringe 100 to allow the drip guard 10 to slide along the exterior of the syringe 100. In certain embodiment, the interior surface of the drip guard 10 may have a lubricous surface or coating to facilitate sliding of the drip guard 10 along the syringe sidewall 102. Using this type of connection, a seal is formed between the inner surface 14 of the drip guard 10 and the sidewall 102 of the syringe 100. The inner diameter of the drip guard 10 may be slightly smaller than the outer diameter of the syringe 100 to create a tight, secure connection between the drip guard 10 and the syringe 100. According to various aspects, the drip guard 10 may be made from an elastic material so as to add flexibility in sliding down the syringe 100. The drip guard 10 may be positioned at any location along the longitudinal axis of the syringe 100. It is also contemplated that more than one drip guard 10 may be provided on the syringe 100 to increase the volume of fluid that can be caught from the syringe 100.

In operation, as the plunger 110 is moved towards the distal end 104 of the syringe 100, fluid is delivered from the syringe 100. Occasionally, fluid may leak or drip down the outer surface of the sidewall 102 of the syringe 100. If no collection or absorption means are in place to catch and/or absorb the fluid, the fluid may be directed into the injector components. Therefore, the drip guard 10 is used to collect and/or absorb any fluid as it flows down the outer sidewall 102 of the syringe 100. Likewise, as fluid is aspirated into the syringe 100, similar fluid drips or leakage may occur.

Figure 6:
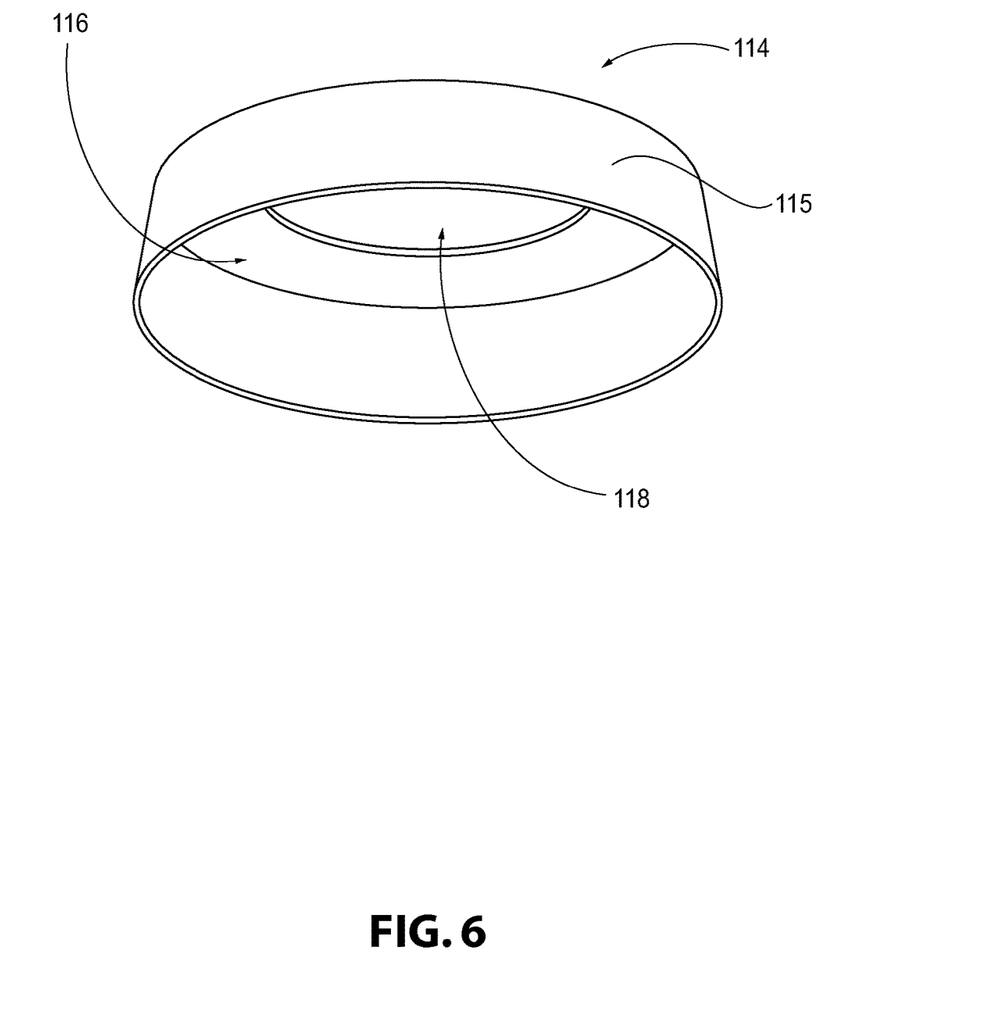
FIG. 6 is a bottom perspective view of a fluid drip trap according to one aspect of this disclosure.
Figure 7:
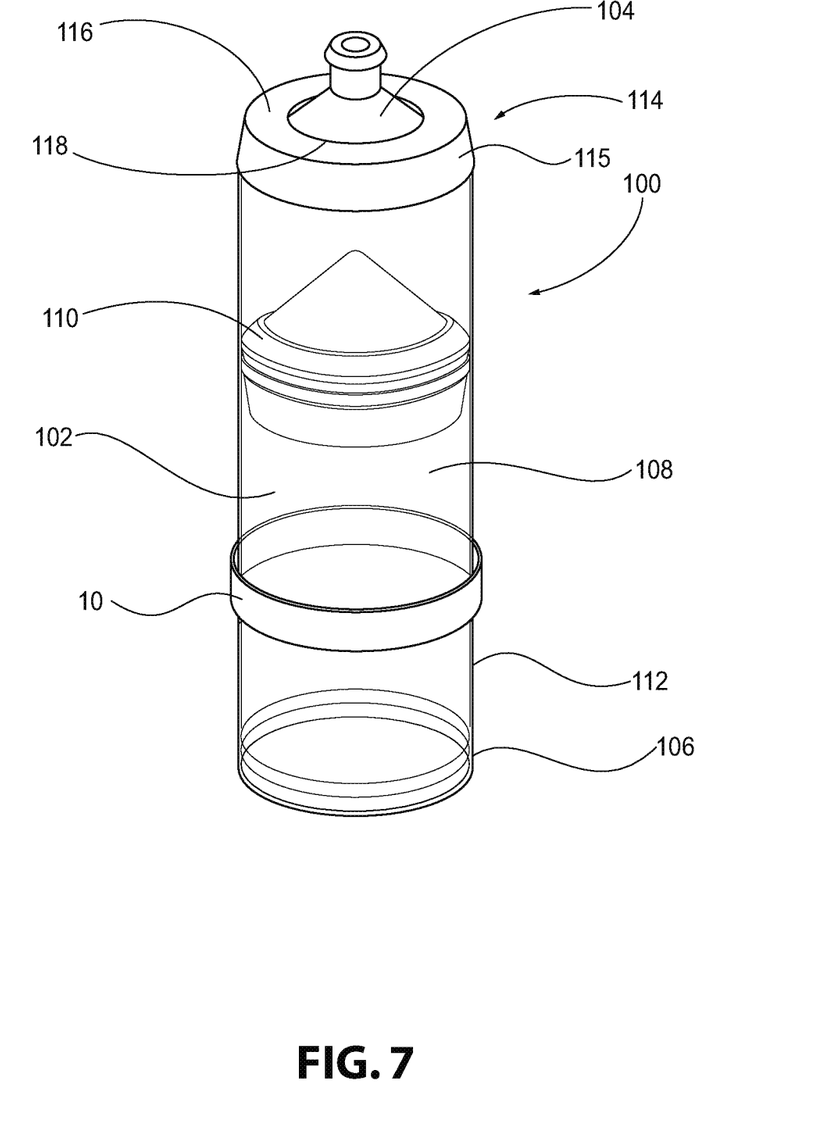
FIG. 7 is a perspective view of a syringe assembly according to another aspect of this disclosure including the fluid drip trap of FIG. 6.

Referring to FIGS. 6 and 7, in another aspect, a fluid drip trap 114 may be provided on the distal end 104 of the syringe 100. According to these aspects, the fluid drip trap 114 may have a circular-shaped wall 115 extending circumferentially around and distally from the distal end of the syringe 100 and having a diameter and cross-sectional shape corresponding approximately to that of the sidewall 102 of the syringe 100. The fluid drip trap 114 may also define an aperture 118 through which the distal end 104 of the syringe 100 may be inserted and allow access to the syringe tip for attachment of a fluid path set or other tubing. For example, in certain aspects, the fluid drip trap 114 may include a sleeve (not shown) that fits partially over and extends proximally from the distal end 104 of the syringe wall 102. The wall 115 of the fluid drip trap 114 may be substantially parallel to that of syringe sidewall 102 or may be angled toward the tip of the syringe 100. The fluid drip trap 114 may be open-ended to allow any medical fluid that leaks from the distal end 104 of the syringe 100 to drain into fluid drip trap 114 through the aperture 118. A seal may be created between the interior wall of fluid drip trap 114 and the distal end 114 of the syringe 100 or distal end of syringe sidewall 102 to prevent fluid from leaking past the fluid drip trap 114. According to certain aspects, a cover 116 may also be provided on the open end of the fluid drip trap 114. The shape of the cover 116 generally corresponds to the shape of the fluid drip trap 114 and defines an aperture 118 therein through which the tip of syringe 100 may extend. The cover 116 may be used to further keep the medical fluid stored in the fluid drip trap 114 from leaking from the fluid drip trap 114 when the distal end of the syringe 100 is pointed in a generally downward direction, for example during certain injection procedures. The cover 116 may be integral with the fluid drip trap 114 or removably attached to the fluid drip trap 114 to permit removal of the cover 116 and emptying of the medical fluid from the fluid drip trap 114 into a suitable waste receptacle. When the cover 116 is installed on the fluid drip trap 114, a gap is defined between the aperture 118 of the cover 116 and the distal end 104 of the syringe 100. This gap allows the leaked medical fluid to flow into the fluid drip trap 114. The fluid drip trap 114 may be integrally molded with, adhered to, or welded to the syringe 100 or removably attached to the syringe 100 via a snap fit, friction fit or interference fit, as described herein The various embodiments of the drip guards or drip traps described herein provide advantages over conventional drip guards. For example, conventional drip guards include a flange extending radially outward from the sidewall of the syringe and are configured to divert fluid dripping down the side of the syringe from dripping directly into the syringe port and fouling the interior workings of the injector. However, the liquid may accumulate on the distal surface of the flange and may drip onto other components of the injector, drip onto the floor, or may come into contact with the skin of the technician while they operated or remove the syringe from the injector. By incorporating an adsorbent material into the drip guard or drip traps, as described herein, any fluid that contacts the drip guard/trap is adsorbed and cannot drip out of the guard/trap or otherwise contact surfaces.

Further, such conventional drip guards protrude radially outward from the outer circumference of the syringe by up to 1 cm or more, thereby increasing the volume requirements of any packaging material to compensate for the added space of the drip guard. Further, the shape of the drip guard may provide the outer surface of the syringe with a non-uniform diameter having a larger profile, further complicating and adding to packaging concerns. In addition, the protruding drip guards may tear flexible packaging materials, such as plastic, by friction or movement during packaging and shipping, resulting in loss of sterility. According to various embodiments herein, the drip guards and drip traps described herein provide improved packaging and shipping concerns by decreasing the 3-dimensional profile of the syringe. For example, as seen in FIGS. 5 and 7, syringes having drip guards or traps as described herein have a more uniform cylindrical profile, such that the syringes may be more closely packaged in primary (individual packaging material) and secondary (multiple unit packaging) packaging material and require less space during shipping, thereby reducing the overall amount of packaging material used and reducing costs associated with shipping.

While aspects of a syringe drip guard were provided in the foregoing description, those skilled in the art may make modifications and alterations to these aspects without departing from the scope and spirit of the disclosure.

The invention claimed is:

1. A syringe assembly, comprising:
   a syringe having a distal end, a proximal end, and a sidewall extending between the distal end and the proximal end; and
   a syringe drip guard monolithically formed with the sidewall and extending around at least a circumferential portion of the sidewall between the distal end and the proximal end of the syringe, the syringe drip guard comprising:
      an outer wall protruding radially outward relative to the sidewall of the syringe; and
      a channel defined between the outer wall of the syringe drip guard and the sidewall of the syringe, the channel having a closed proximal end and an open distal end,
   wherein an inner distal edge of the outer wall is beveled toward the channel,
   wherein the inner distal edge is configured proximal to the distal end of the syringe to assist in the collection of a fluid within the channel, and
   wherein the syringe drip guard is configured to at least one of collect, absorb, and adsorb the fluid within the channel.

2. The syringe assembly of claim 1, wherein the outer wall of the syringe drip guard extends from near the proximal end of the syringe towards the distal end of the syringe such that the outer wall is angled relative to a longitudinal axis of the syringe.

3. The syringe assembly of claim 1, wherein the syringe drip guard further comprises a bottom surface that connects a proximal end of the outer wall to the sidewall of the syringe.

4. The syringe assembly of claim 1, wherein the syringe drip guard further comprises an adsorbent material within the channel for adsorbing the fluid within the channel.

5. The syringe assembly of claim 1, wherein the syringe drip guard is made from a flexible material.

6. The syringe assembly of claim 1, wherein the outer wall of the syringe drip guard extends from near the proximal end of the syringe towards the distal end of the syringe such that the outer wall is substantially parallel to a longitudinal axis of the syringe.

* * * * *

UNITED STATES PATENT AND TRADEMARK OFFICE
CERTIFICATE OF CORRECTION

PATENT NO. : 10,549,043 B2
APPLICATION NO. : 15/317241
DATED : February 4, 2020
INVENTOR(S) : Sams et al.

It is certified that error appears in the above-identified patent and that said Letters Patent is hereby corrected as shown below:

In the Specification
In Column 5, Line 57, delete "distal end 114" and insert -- distal end 104 --, therefor.
In Column 7, Line 49, delete "inner surface 14" and insert -- inner surface 14' --, therefor.
In Column 8, Line 24, delete "distal end 114" and insert -- distal end 104 --, therefor.

Signed and Sealed this
Twenty-sixth Day of May, 2020

Andrei Iancu
*Director of the United States Patent and Trademark Office*